United States Patent [19]

Yang et al.

[11] Patent Number: 6,002,021

[45] Date of Patent: Dec. 14, 1999

[54] PROCESS FOR PREPARING 6(R)-{2-8'(S)-2", 2"-DIMETHYLBUTYRYLOXY-2'(S)-6'(R)-DIMETHYL-1',2',6'7',8'8'A(R)-HEXAHYDRONAPTHYL-1'(S)-ETHYL}-4(R)-HYDROXY-3,4,5,6-TETRAHYDRO-2H-PYRAN-2-ONE

[75] Inventors: Yuh-Lin Yang, Hsinchu Hsien; Yeuk-Chuen Liu, Hsinchu, both of Taiwan

[73] Assignees: Industrial Technology Research Institute, Hsinchu; Yung Shin Pharmaceutical Ind. Co Ltd., Taichung Hsien, both of Taiwan

[21] Appl. No.: 09/106,278

[22] Filed: Jun. 29, 1998

[51] Int. Cl.$^6$ .................................................. C07D 309/30
[52] U.S. Cl. ............................................................ 549/292
[58] Field of Search ............................................... 549/292

[56] References Cited

U.S. PATENT DOCUMENTS

| 4,857,547 | 8/1989 | Hoffman et al. | 549/292 |
| 4,970,231 | 11/1990 | Lee et al. | 549/292 |
| 5,159,104 | 10/1992 | Dabora et al. | 549/292 |

*Primary Examiner*—Amelia Owens
*Attorney, Agent, or Firm*—Sughrue, Mion, Zinn, Macpeak & Seas, PLLC

[57] ABSTRACT

An acylation process using a sulfonic acid, a salt of the sulfonic acid, or a mixture thereof, as a catalyst. Compound 6 is prepared by protecting the 4-hydroxyl group on the pyranone ring of the 8'-hydroxy compound 2 to form a β-protected compound 3, acylating the 8-hydroxy group on the polyhydronaphthyl ring of compound 3 to give protected ester, compound 4, then removing the protecting group, where the compounds 6, 2, 3 and 4 are as described in the specification.

18 Claims, No Drawings

PROCESS FOR PREPARING 6(R)-{2-8'(S)-2",2"-DIMETHYLBUTYRYLOXY-2'(S)-6'(R)-DIMETHYL-1',2',6'7',8'8'A(R)-HEXAHYDRONAPTHYL-1'(S)-ETHYL}-4(R)-HYDROXY-3,4,5,6-TETRAHYDRO-2H-PYRAN-2-ONE

BACKGROUND OF THE INVENTION

1. Field of the Invention

The present invention relates to a process for preparing an antihypercholesterolemia agent, simvastatin, and in particular to a process for preparing simvastatin.

2. Description of Related Art

Antihypercholesterolemia agents such as simvastatin (compound 6), 6(R)-{2-8'(S)-2",2"-dimethylbutyryloxy-2'(S)-6'(R)-dimethyl-1',2',6',7',8'8'a(R)-hexahydro-napthyl-1'(S)-ethyl}-4(R)-hydroxy-3,4,5,6-tetrahydro-2H-pyran-2-one are strong inhibitors of the biosynthesis of cholesterol. Simvastatin is prepared from the raw material lovastatin (compound 1). The 8'-ester group on the polyhydronaphthyl ring of the raw material, lovastatin 1, is hydrolyzed to form an 8'-hydroxy derivative 2. The 4-hydroxyl group on the lactone ring of 2 is then protected with t-butyldimethylchlorosilane in an inert atmosphere at ambient temperature in the presence of an acid acceptor such as imidazole to form a β-protected compound 3. The 8'-hydroxy group on the polyhydronaphthyl ring of compound 3 is then acylated to provide protected ester, compound 4. After removal of the silyl protecting group, the desired product 6, sinvastatin is obtained. The reaction scheme of the above process is indicated below.

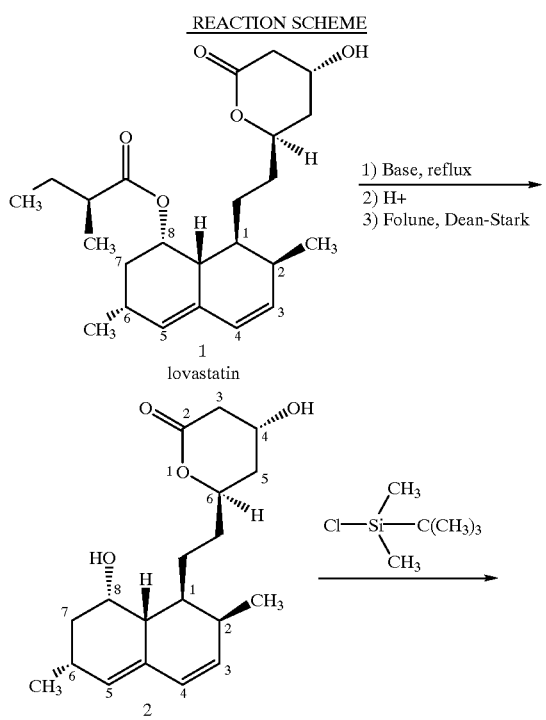

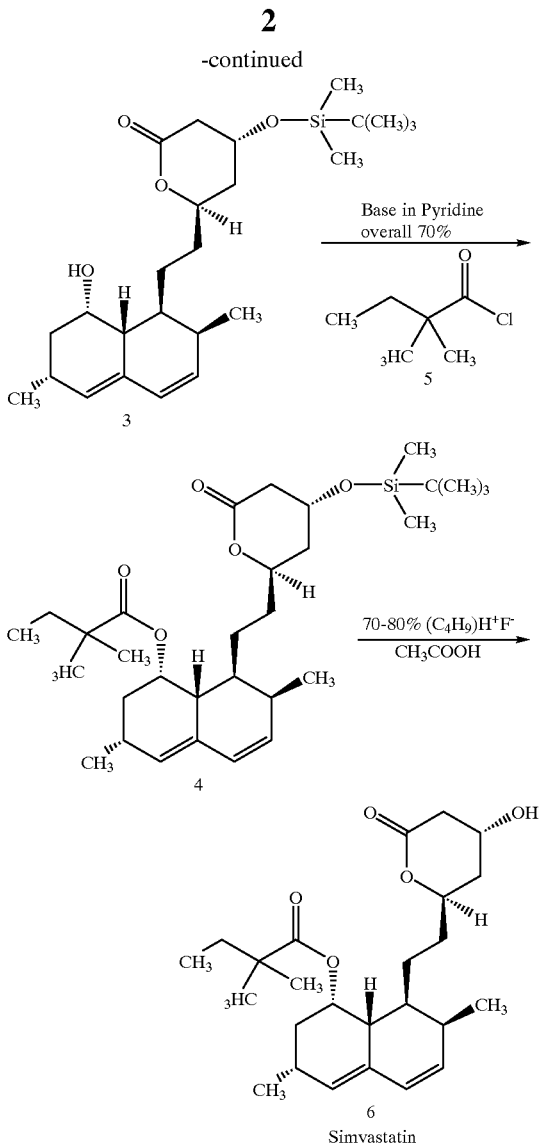

Since compound 3 is highly sterically hindered, acylation of 3 is cumbersome. U.S. Pat. No. 4,845,237 discloses an acylation process involving treatment of the desired acyl group with acid chloride in pyridine in the presence of 4-4-dimethylaminopyridine (DMAP) and lithium bromide as catalysts. U.S. Pat. No. 4,444,784 discloses an acylation process comprising treatment of the 8'-polyhydronaphthol with the free acid of the desired acyl group in the presence of N', N'-dicyclohexylcarbodimide with 4-pyrrolidino-pyridine as a catalyst in dichloromethane.

The two acylation processes require prolonged high reaction temperatures (100° C., 4 hours) and a large quantity of acyl chloride (usually more than 4 equivalents). The formation of a significant amount of side product and the acyl chloride remaining, causes a poor yield in the recovery of the acylated product. On the other hand, the hygroscopic alkali metal bromide (i.e., lithium bromide) requires special treatment and handling.

SUMMARY OF THE INVENTION

It is therefore an object of the present invention to provide a process for preparing simvastatin, compound 6, capable of eliminating the disadvantages of the prior art.

The process of the invention features using an organic sulfonic acid, a salt thereof, or a mixture thereof, as a catalyst in the acylation step of compound 3.

According to the invention, the sulfonic acid or salts thereof can form a mixed anhydride of the sulfonic acid and carboxylic acid in situ, to facilitate the acylation. The amount of acyl chloride used and the production of side product can thus be reduced.

According to the invention, the conversion of compound 3 can reach 98% and the acylation can be completed within 7–8 hours.

Specifically, the process of the invention includes protecting the 4-hydroxy group on the pyranone ring of a compound of the following formula II:

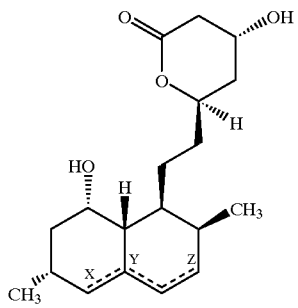

(II)

wherein the dotted lines x, y and z represent possible double bonds, these bonds, when any are present, being either x and z in combination or one of x, y or z alone; R1, R2, R3, R4 and R5 are each independently a C1–C10 alkyl group;

to form a compound III of the following formula:

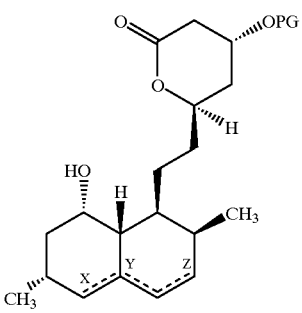

(III)

wherein PG is a protecting group wherein PG is a protecting group of trialkylsilyl or alkyldiarylsilyl, wherein the alkyl has from 1 to 10 carbon atoms and the aryl has from 6 to 10 carbon atoms; preferably, PG is t-butyl-dimethyl-silyl (TBDMS), reacting the compound (III) with a compound having the following formula (V):

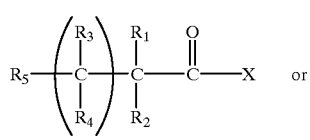

(V)

-continued

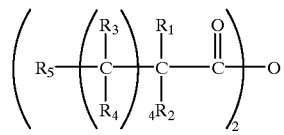

wherein X is a halogen atom, R1, R2, R3, R4, and R5 are each independently a C1–C10 alkyl group, in the presence of an organic sulfonic acid, a salt thereof, or a mixture thereof, to yield an acylation product of the following formula (IV):

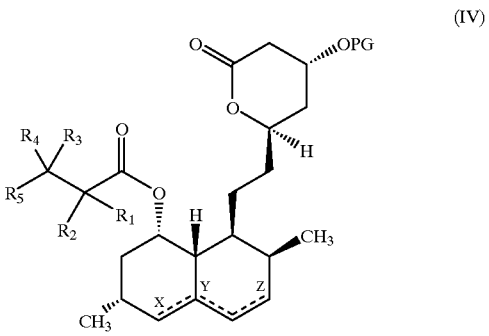

(IV)

wherein PG is a protecting group of trialkylsilyl or alkyldiarylsilyl, wherein the alkyl has from 1 to 10 carbon atoms and the aryl has from 6 to 10 carbon atoms, and deprotecting the protected 4-hydroxy group on the pyranone ring of the acylation product (IV) to produce compound (VI).

DETAILED DESCRIPTION OF THE INVENTION

According to the invention, the catalyst of the acylation is a sulfonic acid, its salts, or a mixture of the sulfuric acid and the salts thereof. Examples of suitable sulfonic acids include, but are not limited to trifluoromethane sulfonic acid and methane sulfonic acid. Examples of suitable salts of sulfonic acids include, but are not limited to pyridinium trifluoromethane sulfonate and silver trifluormethane sulfonate. In case a sulfonic acid or a mixture of sulfonic acid and its salts is used, the amount of the sulfonic acid or its mixture should be 0.01–0.3 molar equivalents per equivalent of compound (III). When salts of the sulfonic acid are used, the amount of the salts should be 0.01–0.05 molar equivalent per equivalent of compound (III). The duration of the acylation using the catalyst of the invention can be reduced to 7–8 hours and the conversion is usually higher than 98%. Also according to the invention, the acylation can be carried out at a relative lower temperature, for example at a temperature of 80° C. to 90° C.

The following specific examples are intended to demonstrate the invention more fully without limiting its scope, since numerous modifications and variations will be apparent to those skilled in this art. Unless otherwise indicated, all parts, percents, ratios and the like are by weight.

EXAMPLE 1

Preparation of Compound 3

Compound 2, 6(R)-{2-8'(S)-Hydroxy-2'(S), 6'(R)-dimethyl-1',2',6',7',8'8'a (R-hexahydronapthhyl-1'(S)-ethyl}-4(R)-hydroxy-3,4,5,6-tetrahydro-2H-pyran-2-one (72 g, 0.225 mole) was dissolved in DMF (285 ml) under a nitrogen atmosphere in a dry reaction flask. DMAP (0.275 g, 0.0023 mole), TEA (63 ml), tert-butyldimethy silylchloride (50.6 g, 0.338 mole) were then added at room temperature and stirred for 7 hours. Water was then added slowly in an ice bath until a precipitate formed. A large amount of water was then added and agitated to obtain a mixture. The mixture was filtered. The precipitate was dissolved in ethyl acetate and washed with water. The organic layer was dried over anhydrous sodium sulfate, filtered and concentrated. After a small amount of ethyl acetate was removed, n-hexane was added. A solid was precipitated. After filtration, concentration, and recrystallization with n-hexane, compound 3 as a white solid was obtained (81.5 g). The yield was 83.4%.

Spectral Data

1H NMR (CDCl3, 400 MHz)(: 0.05 (s,6,(CH3)2, Si), 0.86 (s, 9,(CH3)3CSi), 0.89(d,3,J=8.5 Hz, CH3), 1.16(d,3,J=7.7 Hz, CH3),1.44–2.36 (a series of multiplet), 2.56 (m,2,pyran C-3H), 4.22(m,1, pyran C-4H), 4.27(m,1,naphthalene C-8H),4.66(m,1,pyran C-6H), 5.52 (m, 1,naph C-5), 5.78 (dd, 1, J=6.1, 9.6 Hz, napth C-3H), 5.96 (d,1,J=9.6 Hz, napth C-4H).

Preparation of Compound 4

Compound 3 (53 g, 0.122 mole), pyridinium trifluoromethane sulfonate (0.28 g, 0.0012 mole), pyridine (57 ml) and C2H4Cl2 (260 ml) were added into a dry reaction flask under a nitrogen atmosphere to form a mixture. The mixture was then cooled in an ice bath for about 5–10 minutes, acyl chloride 5 (30 ml, 0.244 mole) was added, and heated to 85° C. until the reaction was completed (9 hours). The reaction product was then cooled to room temperature, washed with 1N hydrochloric acid (100 ml), a saturated aqueous solution of sodium hydrocarbonate (100 ml), and brine (100 ml). The organic layer was dried over anhydrous sodium sulfate, filtered and concentrated to dryness, giving compound 4 (g).

Spectral Data

1H NMR (CDCl3, 200 MHz) (: 0.08(s,6, (CH3)2Si), 0.88(s,9, (CH3)3CSi), 1.08(d, 3,J=7.4 Hz, CH3), 1.12(s, 3,CH3), 1.13(s,3,CH3), 1.87–2.44(a series of multoplet), 2.59 (m, 2 pyran C-3H), 4.28 (m, 1, pyran C-4H), 4.58 (m, 1, pyran C-6H), 5.34 (m, 1,napththalene C-8H), 5.51 (bt, 1,napth C-5H), 5.77 (dd, J=6.0, 9.6 Hz, naph C-3H), 5.99 (d,1,J=9.6 Hz, naph C-4H)

Preparation of Compound 6

The reaction mixture of the above acylation mixture was dissolved in acetonitrile (252 ml). An aqueous solution of methyl sulfonic acid (39% v/v, 0.146 mole) was added and stirred at room temperature (about 20–30° C.) for 4 hours. An aqueous solution of sodium hydroxide (360 ml, 1N) was then added to the reaction mixture and the mixture was stirred at room temperature for a further 12 hours. The reaction mixture was then cooled with an ice bath, acidified with 3N hydrochloric acid to pH 3–4 and extracted with ethyl acetate twice. After being concentrated under reduced pressure to 150–200 ml, ammonium hydroxide in methanol was added dropwise and the mixture was cooled with an ice bath at 4° C. for 2 hours. After filtration, the ammonium salt of simvastatin (compound 6, 34.7 g) was obtained. The ammonium salt was then heated in toluene (800 ml) under a nitrogen atmosphere at 100° C. for 5 hours. After being concentrated under a reduced pressure, cyclohexane (100 ml) was added and again the mixture was concentrated under a reduced pressure to give a semi-solid. After recrystallization with cyclohexane, simvastatin (25.3 g) was obtained. The combined mother liquid was chromatographied (silica gel, ethyl acetate;n-hexane+1:1) to give simvastatin 6 (13.5 g). The total yield was 77%.

Spectral Data

1HNMR (CDCl3, 400 MHz): 0.83(t, =7.4 Hz, C-4"H) 0.89(d,3,J=7.1 Hz, CH3), 1.08(d,3,J=7.4 Hz, CH3), 1.12(s, 3,CH3), 1.139s,3,CH3), 1.24–2.36(a series of multiplet), 2.77–2.63 (m,2,pyran C-3H), 4.389 m, 1, pyran C-4H), 4.61 9 m, 1, pyran C-6H), 5.37 (m, 1, naphthalene C-8H), 5.51 (bt, 1, napth C-5H), 5.78(dd, 1, J=6.1, 9.6 Hz, napth C-3H), 5.99 (d, 1, J=9.6 Hz, napth C-4H).

While the invention has been described in detail and with respect t various embodiments thereof, it will be apparent to one skilled in the art that various changes and modifications can be made therein without departing from the spirit and scope thereof.

What is claimed is:

1. A process of preparing a compound of the following formula (VI):

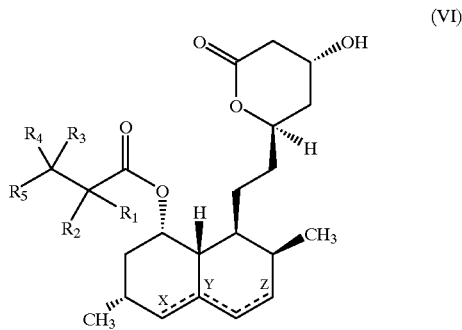

(VI)

wherein the dotted lines x, y and z represent possible double bonds, said bonds, when any are present, being either x and z in combination or one of x, y or z alone;

wherein $R_1$ and $R_2$ are independently a hydrogen atom or a C1–C10 alkyl group, or $R_1$ and $R_2$ together with the carbon atom to which they are attached form a carbocyclic ring of 3 to 8 carbon atoms;

$R_1$, $R_2$, $R_3$, $R_4$ and $R_5$ are each independently a hydrogen atom or a C1–C10 alkyl group; comprising the following steps:

(1) protecting the 4-hydroxy group on the pyranone ring of a compound of the following formula (II):

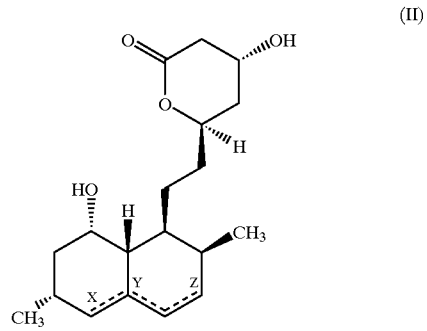

(II)

wherein x, y and z are defined as above to form a compound III of the following formula:

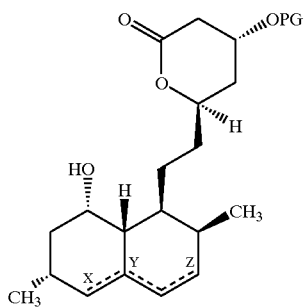

(III)

wherein PG is a protecting group of trialkylsilyl or alkyldiarylsilyl, wherein the alkyl has from 1 to 10 carbon atoms and the aryl has from 6 to 10 carbon atoms;

(2) reacting compound (III) with a compound having the following formula (V) or (V'):

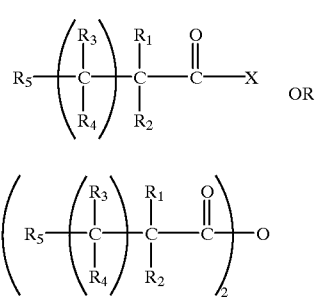

wherein X is a halogen atom, $R_1$, $R_2$, $R_3$, $R_4$ and $R_5$ are each independently a C1–C10 alkyl group, in the presence of an organic sulfonic acid, a salt thereof, or a mixture thereof, to yield an acylation product of the following formula (IV):

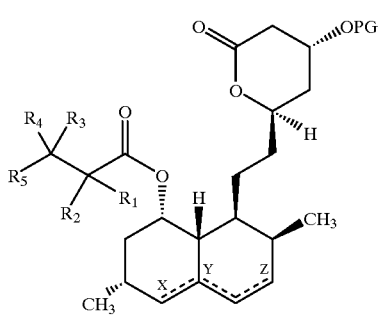

(IV)

wherein PG is defined as above, (3) deprotecting the protected 4-hydroxy group on the pyranone ring of the acylation product (IV) to produce said compound (VI).

2. The process as claimed in claim 1, wherein the sulfonic acid is trifluoromethane sulfonic acid.

3. The process as claimed in claim 1, wherein said salt of sulfonic acid is pyridinium trifluoromethane sulfonate.

4. The process as claimed in claim 1, wherein in step (2) sulfonic acid is present in an amount of 0.1–0.3 molar equivalents per molar equivalent of said compound(III).

5. The process as claimed in claim 1, wherein in step (2) the salt of said sulfonic acid is present in an amount of 0.01–0.05 mole equivalents per molar equivalent of said compound (III).

6. The process as claimed in claim 1, wherein in the reacting step (2) the process comprises reacting at a temperature of 80° C. to 90° C.

7. The process as claimed in claim 1, wherein compound (V) is present in an amount of 2–4 molar equivalents per molar equivalent of said compound (III).

8. The process as claimed in claim 1, wherein compound (V) or (V') is an acyl chloride of the formula (V).

9. A process of preparing a compound of the following formula (IV):

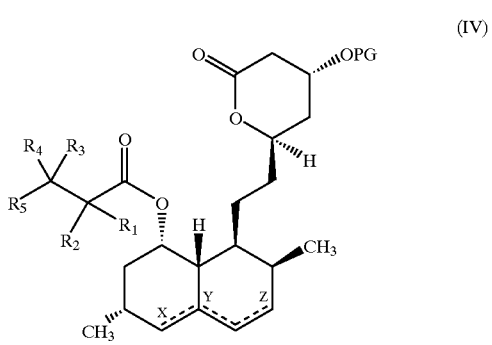

(IV)

wherein the dotted lines x, y and z represent possible double bonds, said bonds, when any are present, being either x and z in combination or one of x, y or z alone, and PG is a protecting group of trialkylsilyl or alkyldiarylsilyl, wherein the alkyl has from 1 to 10 carbon atoms and the aryl has from 6 to 10 carbon atoms;

wherein $R_1$ and $R_2$ are independently a hydrogen atom or a C1–C10 alkyl group, or $R_1$ and $R_2$ together with the carbon atom to which they are attached form a carbocyclic ring of 3 to 8 carbon atoms; and $R_1$, $R_2$, $R_3$, $R_4$ and $R_5$ are each independently a hydrogen atom or a C1–C10 alkyl group; comprising the following steps:

(1) protecting the 4-hydroxy group on the pyranone ring of a compound of the following formula (II):

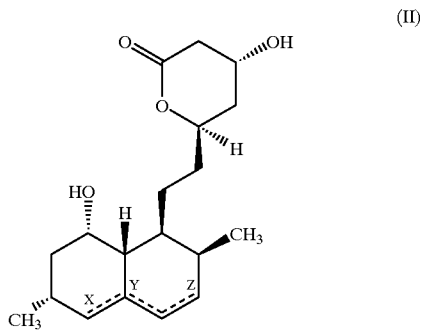

(II)

wherein x, y and z are defined as above to form a compound III of the following formula:

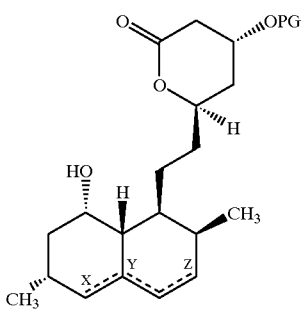

(III)

wherein PG is a protecting group of trialkylsilyl or alkyldiarylsilyl, wherein the alkyl has from 1 to 10 carbon atoms and the aryl has from 6 to 10 carbon atoms;

(2) reacting compound (III) with a compound having the following formula (V) or (V'):

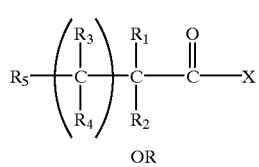

(V)

OR

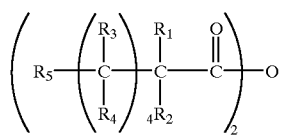

(V')

wherein X is a halogen atom, $R_1$, $R_2$, $R_3$, $R_4$ and R5 are each independently a hydrogen atom or a C1–C10 alkyl group, in the presence of an organic sulfonic acid, a salt thereof, or a mixture thereof, to yield an acylation product of the formula (IV).

10. The process as claimed in claim 9, wherein the sulfonic acid is trifluoromethane sulfonic acid.

11. The process as claimed in claim 9, wherein said salt of sulfonic acid is pyridinium trifluoromethane sulfonate.

12. The process as claimed in claim 9, wherein in step (2) the sulfonic acid is present in an amount of 0.1–0.3 molar equivalents per molar equivalent of said compound (III).

13. The process as claimed in claim 9, wherein in step (2) the salt of said sulfonic acid is present in an amount of 0.01–0.05 mole equivalents per molar equivalent of said compound (III).

14. The process as claimed in claim 9, wherein in the reacting step (2) the process comprises reacting at a temperature of 80° C. to 90° C.

15. The process as claimed in claim 9, wherein the amount of compound (V) is 2–4 molar equivalents per molar equivalent of said compound (III).

16. The process as claimed in claim 9, wherein compound (V) or (V') is an acyl chloride.

17. The process as claimed in claim 1, wherein the protecting group PG is t-butyl-dimethyl-silyl.

18. The process as claimed in claim 9, wherein the protecting group PG is t-butyl-dimethyl-silyl.

* * * * *